United States Patent [19]

Christians et al.

[11] Patent Number: 5,290,749
[45] Date of Patent: Mar. 1, 1994

[54] PREEMERGENCE WEED CONTROL USING PLANT PORTEIN HYDROLYSATE

[75] Inventors: Nick E. Christians, Ames; John T. Garbutt, Muscatine; Dianna Liu, Ames, all of Iowa

[73] Assignees: Iowa State University Research Foundation, Inc., Ames; Grain Processing Corporation, Muscatine, both of Iowa

[21] Appl. No.: 101,431

[22] Filed: Aug. 3, 1993

[51] Int. Cl.⁵ .............................................. A01N 65/00
[52] U.S. Cl. ..................................... 504/189; 504/335
[58] Field of Search ....................... 504/116, 189, 335; A01N 65/00

[56] References Cited

U.S. PATENT DOCUMENTS 3,161,497 12/1964 Amburn .................................. 504/116
5,030,268 7/1991 Christians .............................. 504/189

FOREIGN PATENT DOCUMENTS 294168 9/1991 Fed. Rep. of Germany .
61-200901 9/1986 Japan .
2-231405 9/1990 Japan .

*Primary Examiner*—Glennon H. Hollrah
*Assistant Examiner*—S. Mark Clardy
*Attorney, Agent, or Firm*—Merchant, Gould, Smith, Edell, Welter & Schmidt

[57] ABSTRACT

A method of selectively inhibiting growth of unwanted plants in a plot of soil is provided comprising the application of a plant protein hydrolysate to the plot of soil, prior to emergence of the unwanted plants and at a concentration of application which inhibits the growth of the unwanted plants.

23 Claims, No Drawings

PREEMERGENCE WEED CONTROL USING PLANT PORTEIN HYDROLYSATE

BACKGROUND OF THE INVENTION

Herbicides have been widely employed to destroy unwanted plants or "weeds", to prevent their growth on bare ground or in established crops, and to promote the growth of desirable plants, such as grains, fruits and vegetables. In fact, millions of pounds of herbicide are applied directly to the soil on an annual basis. In general, herbicides consist of two types, non-selective and selective. Non-selective herbicides kill all plant life on the plot of soil on which they are applied. Selective herbicides, on the other hand, kill or inhibit the establishment of certain types of plant life, such as weeds, while leaving the desirable, surrounding crops on which they are applied relatively undamaged. Examples of selective herbicides include phenolics, carbamates, and dinitroanilines.

One way to selectively eliminate unwanted plants without injuring surrounding plant life is to inhibit germination or establishment of the seeds of the unwanted plants. In order to accomplish this, a herbicide must be applied before the unwanted plants emerge from the soil, either to a bare plot of soil into which established plants will be transplanted, or to a plot of soil comprising an established stand of desirable plants, but relatively few weeds. Such herbicides are often referred to as preemergence herbicides.

While various types of herbicides exist, most of them are based on synthetic chemical toxins. As a result of their toxic nature, they are undesirable for many applications. In general, herbicides must be applied over large areas of crops intended for human consumption. Therefore, while synthetic chemical herbicides may effectively destroy unwanted plant life, they may contaminate the soil and the crops themselves. They may also contaminate the ground water as a result of run off or erosion.

The disadvantages of synthetic chemical herbicides have become more visible as a result of heightened public awareness and concern for environmental protection and consumer safety. This in turn has led to the search for non-toxic, natural herbicides which can provide a greater margin of safety for the public and for the environment. In the area of herbicides or insecticides, however, few effective materials derived from naturally-occurring sources are known. *Bacillus thuriqiensis* (Bt toxins), *Bacillus popilliae, Serratia eritomophila, Puccinia chondrillina,* and *Sclerotinia sclerotiotum* represent some examples of natural herbicides and insecticides that currently exist. Corn gluten meal is capable of inhibiting root growth of germinated seed, while no damage is observed to plants that have formed a mature root system. Christians (U.S. Pat. No. 5,030,268) discloses that this material is useful as a natural preemergence herbicide for various plant production systems, including turfgrass areas, where it acts to inhibit the establishment of annual weeds, such as crabgrass (*Digitaria spp.*).

Corn gluten meal, however, is essentially water-insoluble. This characteristic limits its use as an herbicide for some applications. Since corn gluten meal is insoluble and cannot be dissolved and sprayed, it is difficult to apply evenly. As a result, there is a risk that the soil on which it is applied will not be completely covered, thereby significantly reducing its effectiveness. Also, sprayable herbicides are advantageous for application to certain crops.

Therefore, a continuing need exists for potent, natural preemergence herbicides which are also highly water dispersible and/or water soluble.

SUMMARY OF THE INVENTION

This invention provides a selective, non-toxic preemergence herbicide for use on soil plots to control both broadleaf and grassy weeds. Plant protein hydrolysates, preferably selected from the group consisting of corn gluten hydrolysate, wheat gluten hydrolysate, soy protein hydrolysate and mixtures thereof, have been found to provide water-soluble materials which are at least as active as corn gluten meal as preemergence herbicides. For example, dry corn gluten hydrolysate prepared as disclosed hereinbelow has been observed to completely stop root formation of test species at an application level of 0.24 $g/dm^2$ in controlled environmental chambers in the laboratory and has been observed to prevent plant establishment by 96% at a level of 1.72 $g/dm^2$ in greenhouse trials on soil.

The examples hereinbelow demonstrate that corn gluten hydrolysate, wheat gluten hydrolysate and soy protein hydrolysate can be used as a growth-regulating material to inhibit root formation of germinating weeds in agricultural end-use settings. These hydrolysates can also be used safely with both broadleaf and grassy crops, and thereby act as natural preemergence herbicides. The plant protein hydrolysates can be applied to a plot of soil prior to transplanting the desirable plants, or can be applied to a plot of soil which already has a stand of established desirable plants thereon. Because these materials are protein hydrolysates of natural plant materials, they should be useful products for use in agriculture as a substitute for synthetic herbicides.

As used herein, the term "plot of soil" is intended to broadly cover volumes of solid plant support material such as the mixture of organic and inorganic materials conventionally referred to as "soil," as well as synthetic soils (or "soiless soils") and homogeneous solid supports such as beds of pebbles, sand, moss and the like. The solid plant support material may be potted, or otherwise contained, or may be a preselected portion of the ground.

Although the present invention has been exemplified primarily by reference to corn, wheat and soy hydrolysates, due to the similarity in the amino acid compositions of the various plant proteins, it is believed that a wide variety of plant protein hydrolysates would be useful in the practice of the invention, including hydrolysates from other grains and legumes.

DETAILED DESCRIPTION OF THE INVENTION

Corn gluten meal is commercially available as a by-product of corn milling. It is made by drying the liquid gluten stream separated from corn during corn wet milling processing. In the wet milling process of corn, the following fractions are obtained: corn starch, corn oil, defatted corn germ, corn hulls, corn steep liquor, and corn gluten (the protein fraction). Corn gluten is typically separated from the starch stream by centrifugation to yield a thick, yellow slurry of corn gluten containing 15 to 20% solids. Conventionally, corn gluten is filtered and dried to produce solid corn gluten meal, which is sold as an animal feed product. Corn gluten meal is quite insoluble in water and is typically composed of the materials listed in Table I, below.

TABLE 1

| Corn Gluten Meal Component | %, Dry Basis |
|---|---|
| Protein | 60–70 |
| Carbohydrate | 20–25 |
| Fat | 3–5 |
| Ash | 3–5 |

The present plant protein hydrolysates are preferably prepared by a process comprising treating an aqueous slurry of a plant protein such as corn or wheat gluten or soy protein with acid or with one or more enzymes. Preferably, the plant protein is treated with one or more proteases, and most preferably, is pre-treated with one or more amylases. For example, the proteinaceous slurry may be treated with amylases, followed by filtration to remove the solubilized carbohydrates. The insoluble residue is then treated with one or more proteases to solubilize the protein components. After pH adjustment with acid, the slurry is filtered and/or centrifuged. The effluent is dried in a conventional manner to yield "corn gluten hydrolysate", "wheat gluten hydrolysate" or "soy protein hydrolysate", which is essentially water soluble (>90% at 10 g/100 ml).

Alternatively, the protein slurry can be treated with proteases alone and the entire reaction mixture dried, or the reaction mixture may be centrifuged or filtered and the supernatant or filtrate dried in an appropriate manner, to yield a soluble plant protein hydrolysate.

To prepare corn gluten hydrolysates, the liquid corn gluten (15–20% solids) is preferably diluted with water to a solids concentration of about 5 to 20% and the pH adjusted to about 6.0 to 8.0, preferably to about pH 6.5. The appropriate amylase is added (0.1 to 1.0% dry basis (DB)) and the slurry jet cooked at 280° to 340° F., preferably at 320° F. for 3–4 minutes. The cooked slurry is then adjusted to about pH 4 to 5, cooled to 140° F. and, optionally, a saccharifying amylase (glucoamylase) is added (0.01 to 0.1% DB) and the slurry maintained at 140° F. for 8–16 hours, preferably about 12 hours. The slurry is then filtered and washed and the filtrate and washings discarded. The filter cake is reslurried in water to 5 to 20% solids (preferably about 10%) and adjusted to pH 7.5 to 9 with $Ca(OH)_2$. An alkaline protease is then added (0.1% to 1% DB) and the slurry is maintained at 50° to 60° C. for 2 to 6 hours, or until the pH remains constant. The slurry is then adjusted to pH 6.0 to 6.8 (preferably pH 6.2), the precipitated $Ca_3(PO_4)_2$ and any insoluble residue is removed by filtration. The clear filtrate is then dried in an appropriate manner (i.e., spray drying, drum drying, etc.) to yield a dry solid product having greater than about 80–90% protein (Kjeldahl nitrogen), and which is essentially water-soluble at 10 wt-% concentration. On a dry basis, the corn gluten hydrolysate will have a nitrogen content of at least about 8%, i.e., about 8–11.2%, most preferably at least about 14.4%.

The dry product can be applied by the use of conventional spreaders or dusters used for solid fertilizers or herbicides and can be applied as a dust, pellets, granules and the like. Corn gluten hydrolysate can be applied at a level of 0.003–10 g/dm² of soil area, preferably at a level of about 0.5–4 g/dm² of soil area. Corn gluten meal hydrolysate may also be freely dissolved or suspended in water and thus can be readily applied by delivery systems employed for the application of liquid herbicides, such as by spraying and watering. The amount of aqueous plant protein hydrolysate which is applied can be varied over a wide range depending on soil type, field contour, target species and the like. In some cases, it is preferable to combine or mix the corn gluten hydrolysate with the soil.

It is believed that liquid or solid plant protein hydrolysates will be effective to prevent the emergence of a wide variety of undesirable plants, including broadleaf weeds, such as smartweed, velvetleaf, redroot, pigweed, lambsquarters, latchweed bedstraw, black medic, buckhorn plantain, annual purslane, black nightshade; and grassy weeds such as crabgrass, annual bluegrass, creeping bentgrass, barnyard grass, orchard grass, woolly cupgrass, foxtails, shattercane, Kentucky bluegrass, Bermuda grass, perennial ryegrass and tall fescue. Thus, corn gluten hydrolysate, soy protein hydrolysate, or wheat gluten hydrolysate can be used as preemergence herbicides for application to established desirable plants, including both monocotyledonous plants and dicotyledonous plants. Monocotyledonous crops include the grains; corn, sorghum, rice, oats, wheat, rye, millet, turfgrasses and the like. Dicotyledonous crops include fruits, fibers, herbs, vegetables, ornamental flowers and foliage, and legumes, including berry plants such as strawberries, blueberries and raspberries, soybeans, potatoes, spinach, cauliflower, tomatoes, tobacco, beans, beets, cotton, peas, squash, melons, canola and the like.

As recognized by those skilled in the art, it is necessary to apply preemergence herbicides after the emergence or rooting of the desirable plants, but prior to weed emergence. The precise time of application will vary, depending upon the specific crop production system, the area of the country in which the hydrolysate is applied and the weed species involved. For example, in general, for areas of the upper Midwest, application must be prior to May 1 st of any growing season, for control of crabgrass.

The invention will be further described by reference to the following detailed examples.

EXAMPLE 1

Prior to filtration, liquid corn gluten was adjusted to about 14% solids with water and to pH 6.5 with dilute sodium hydroxide to yield 500 ml of the pH-adjusted gluten. Next, 0.07 ml THERMOLASE enzyme (an amylase available from Enzyme Development Corporation, New York, NY) was added. The slurry was jet-cooked while adding steam at 160° C. for 3–4 minutes. To ensure complete liquification of the starch, 0.5 ml of CANALPHA 600 (an amylase from Biocon U.S., Inc., Lexington, Ky.) was added and the slurry held at 80° C. for one hour. The gluten slurry was then cooled to 60° C., and its pH was adjusted to 4.6 with dilute hydrochloric acid. Another enzyme, ZYMETEC 200, 0.2 ml,(a glucoamylase manufactured by Enzyme Technology, Inc., Ashland, Ohio) was added to the slurry and the slurry maintained at 60° C. for 13 hours.

The slurry was filtered through diatomaceous earth and the filter cake was washed with water. The filtrate and washings were discarded, the wet filter cake reslurried in water to about 12% solids and adjusted to pH 8.5 with $Ca(OH)_2$. Then 0.2 ml of the protease enzyme, ALCALASE 2.4L (NOVO Laboratories, Danbury, Conn.) was added while maintaining the reaction mixture at pH 8.5, 55° C for 5 to 8 hours (or until such time that the pH remained constant). Afterwards, dilute phosphoric acid was added to adjust the pH to 6.5 to precipitate the calcium ion as calcium phosphate. The resulting suspension was then heated to 85° C. for 20 minutes to inactivate the enzyme. The solution was filtered and the cake washed with water, followed by combining the washings with the filtrate. The filter cake was discarded.

The clear, brown filtrate containing corn gluten hydrolysate can be spray dried as is, or reduced by evaporation and then spray dried. The resulting dry product, corn gluten hydrolysate has the properties listed in Table II below.

TABLE II

| Appearance | Cream-tan powder |
|---|---|
| Dry substance, % | >90 |
| Solids recovery | >50 |
| Protein, % DB (% Kjeldahl nitrogen × 6.25) | >90 |
| pH (as 5% solution) | >6.5 |
| Water solubility (as 10% w/v solution) | soluble with slight haze |
| Ash, % DB | <5 |
| Odor | characteristic odor |

EXAMPLE 2

Corn gluten hydrolysate was prepared by a simplified procedure which also yields a water-soluble form of lower protein content.

As in Example 1, the liquid corn gluten is reconstituted in water, this time to about 10% solids. The slurry (500 ml) was then adjusted to pH 8.5 with a 10% slurry of calcium hydroxide. The protease enzyme, ALCALASE 2.4L, (1.0% dry basis) was added and the solution stirred at 60° C. for 5 to 8 hours, or until such time that the pH remained constant at 8.5.

The material was then processed as described in Example 1, to yield a corn gluten hydrolysate which had the properties shown in Table III, below:

TABLE III

| Appearance | cream-tan powder |
|---|---|
| Dry substance, % | >90 |
| Solids recovery | >50 |
| Protein, % DB (% Kjeldahl nitrogen × 6.25) | >70 |
| pH | 6.5 |
| Water solubility (10% solution) | soluble |
| Ash, % DB | <5 |
| Odor | characteristic odor |

EXAMPLE 3

The procedure of Example 2 was further simplified to yield a solubilized form of corn gluten of somewhat lower protein content by simply following the steps of Example 2, with the exception that the final filtration step was not carried out. After adjustment to a pH of 6.5 with phosphoric acid, the slurry was freeze-dried. The properties of the resulting product are shown on Table IV below:

TABLE IV

| Appearance | cream-tan powder |
|---|---|
| Dry substance, % | >90 |
| Solids recovery % | >95 |
| Protein, % DB (% Kjeldahl nitrogen × 6.25) | >50 >50 |
| Water solubility (10% soln) | >50% of solids |

TABLE IV-continued

| pH | 6.5 |
|---|---|

EXAMPLE 4

A study was conducted in a controlled environment to investigate the effect of the corn gluten hydrolysate of Example 1 on creeping bentgrass and crabgrass. An aqueous dilution of the corn gluten hydrolysate of Example 1 in 7 ml water was applied to blotter paper measuring 42.3 $cm^2$ at levels of 0 $g/dm^2$, 0.12 $g/dm^2$, 0.24 $g/dm^2$, 0.36 $g/dm^2$, and 0.48 $g/dm^2$. Eighteen seeds were placed on the blotter papers which were then put into petri dishes, and placed into a controlled environmental chamber. The chamber was set at a 16 hr photoperiod and maintained at a constant 25° C. Table V illustrates the percentage of germination of the creeping bentgrass and crabgrass with varying application levels of corn gluten hydrolysate of Example 1.

TABLE V

PERCENTAGE OF GERMINATION OF CREEPING BENTGRASS AND CRABGRASS TREATED WITH CORN GLUTEN HYDROLYSATE

| Level of Hydrolysate ($g/dm^2$) | (% germination) | |
|---|---|---|
| | Bentgrass | Crabgrass |
| 0.00 | 61 | 67 |
| 0.12 | 44 | 6 |
| 0.24 | 11 | 0 |
| 0.36 | 0 | 0 |
| 0.48 | 0 | 0 |

As can be seen from Table V, corn gluten hydrolysate completely stopped germination of creeping bentgrass at application levels above 0.24 $g/dm^2$, and completely stopped germination of crabgrass at application levels above 0.12 $g/dm^2$.

EXAMPLE 5

A study was conducted comparing the effect of corn gluten hydrolysates of Examples 1 and 3 on crabgrass in a greenhouse. The crabgrass was seeded at a rate of 0.19 $g/dm^2$ onto 58 $cm^2$ pots filled with a clay loam soil. The hydrolysates of Examples 1 and 3 were applied to the surface of the pots at levels of 0, 0.86, 1.72, 3.44, and 6.88 $g/dm^2$. The pots were then placed on a mist bench for 6 days. After seed germination, if any, the pots were moved to a greenhouse bench and maintained for 15 days. Data were collected on the number of live shoots from each pot. The study was repeated three times.

Table VI illustrates the results of this study.

TABLE VI

THE EFFECT OF TWO CORN GLUTEN HYDROLYSATES ON THE ESTABLISHMENT OF CRABGRASS SEEDLING ON SOIL IN THE GREENHOUSE

| Level of Hydrolysate ($g/dm^2$) | Crabgrass (% of live plants/pot) | |
|---|---|---|
| | Hydrol. (Ex. 1) | Hydrol. (Ex. 3) |
| 0.00 | 95 | 95 |
| 0.86 | 23 | 57 |
| 1.72 | 4 | 21 |
| 3.44 | 0 | 2 |
| 6.88 | 0 | 0 |

As can be seen from Table VI, the corn gluten hydrolysate of Example 1 reduced the establishment of crabgrass by 76%, 96%, 100%, and again by 100% at application levels of 0.86 g/dm², 1.72 g/dm², 3.44 g/dm², and 6.88 g/dm², respectively. The corn gluten hydrolysate of Example 3 reduced the establishment of crabgrass by 40%, 78%, 98% and 100% at the same application levels. Thus, while corn gluten hydrolysate of Example 3 is somewhat less effective than corn gluten hydrolysate of Example 1, it is still highly active.

EXAMPLE 6

In a further study, a comparison was made regarding the effects of corn gluten meal and the corn gluten hydrolysate of Example 1 on the establishment of perennial ryegrass (*Lolium perenne*). Application levels of the dry hydrolysate to the surface of soil pots seeded with *L. perenne* ranged from 0 to 7.8 g/dm². The pots were allowed to stay on the mist bench for a 24-hour period in order to moisten the soil without leaching of the water soluble corn gluten hydrolysate. Table VII provides the results of this study.

TABLE VII

THE EFFECTS OF CORN GLUTEN MEAL (CGM) AND CORN GLUTEN HYDROLYSATE (CGH) ON THE ESTABLISHMENT OF PERENNIAL RYEGRASS

| Application level of CGM and CGMH (g/dm²) | (% Inhibition) | |
|---|---|---|
| | CGM | CGH |
| 0.00 | 0 | 0 |
| 1.3 | 0 | 0 |
| 2.6 | 0 | 60 |
| 3.9 | 0 | 87 |
| 5.2 | 3 | 97 |
| 6.5 | 0 | 100 |
| 7.8 | 10 | 97 |

The above Table demonstrates the increased effectiveness of the corn gluten hydrolysate of Example 1 as compared with corn gluten meal. Treatment with 5.2 g/dm² of the corn gluten hydrolysate of Example 1 resulted in 97% control. The same level of corn gluten meal, however, resulted in only 3% control.

EXAMPLE 7. ACID HYDROLYSIS OF CORN GLUTEN MEAL

Corn gluten meal, 20 g, was placed in a 500 ml round bottomed flask, 230 ml of 2N phosphoric acid added and the mixture was refluxed for 20 hours. The dark slurry was centrifuged and the dark supernatant filtered. The clear brown filtrate (pH 1) was adjusted to pH 6.5 with 31.5 g calcium hydroxide. The precipitate of calcium phosphate was removed by centrifugation and the clear dark supernatant freeze-dried to yield a tan powder containing 91% solids, 68.4% protein, as is, and 6.06% ash, as is. This product was designated acid hydrolysate 1 (AH-1).

EXAMPLE 8. ACID HYDROLYSIS OF THE ENZYME HYDROLYSATE OF CORN GLUTEN

Fifteen grams of corn gluten hydrolysate (prepared as described in Example 1), was placed in a 500 ml round bottom flask and 160 ml of 2N phosphoric acid added. The solution was refluxed 20 hours, filtered with the aid of filteraid, and the clear brown filtrate, pH 1, adjusted to pH 7.5 with 30 grams of calcium hydroxide. The precipitated calcium phosphate was removed by filtration and the clear filtrate freeze-dried to yield a tan powder containing 96.5% dry solids, 82.4% protein, as is, and 7.3% ash, as is. This product was designated acid hydrolysate 2 (AH-2).

EXAMPLE 9. HERBICIDAL ACTIVITY OF ACID HYDROLYSATES

The above two products, AH-1 and AH-2, along with corn gluten hydrolysates, CGH, prepared as described in Example 1, were assayed for their herbicide activity by the following standard laboratory assay procedure. Dilutions were prepared in water of AH-1, AH-2, and CGH to contain 1, 2 and 4 mg./ml. A Whatman No. 1 filter paper disk (7 cm in diameter) was placed in each of several 100×15 mm plastic petri dishes. One ml of each of the hydrolysate dilutions was then distributed uniformly onto the filter paper disks. Then ten perennial ryegrass seeds were distributed uniformly on top of each filter paper disk. The petri dishes were covered, sealed with parafilm, and allowed to stand at about 23° C. for 14 days. A control sample was prepared in the same manner except one ml of water was used.

After 14 days, the length of the individual roots of each seed were determined and the average of the seven longest roots calculated. This value was expressed as a percent of the average root length of the Control. These results are shown in Table VIII, below.

TABLE VIII

The Effects of Acid Hydrolysates of Corn Gluten Meal (AH-1) and Corn Gluten Hydrolysate (AH-2) and CGH on the Establishment of Perennial Ryegrass

| Application Level (mg/dm²) | (% of Control Root Length) | | |
|---|---|---|---|
| | AH-1 | AH-2 | CGH |
| 2.6 | 68 | 50 | 42 |
| 5.2 | 0 | 0 | 0 |
| 10.4 | 0 | 0 | 0 |

As the results show, CGH appears to be slightly more effective in inhibiting root formation than either AH-1 or AH-2 but all hydrolysates completely inhibited root growth at 5.2 mg/dm² and above.

These results further demonstrate that acid treatment can also be used to solubilize the herbicide activity in plant proteins. Those skilled in the art would realize that other acids (i.e., hydrochloric, sulfuric, etc.) under the appropriate conditions could be employed, as well as phosphoric acid, to solubilize the herbicide activity in plant proteins.

EXAMPLE 10

Soy hydrolysate and extracts obtained by the fractionation of soy hydrolysate with an absorptive resin, AMBERLITE XAD-16 (manufactured by Rohm & Haas Company, Philadelphia, Pa.) have also shown to have herbicidal activity. In this example, a soy hydrolysate was prepared by slurrying 100 grams of soy protein in about 900 ml of water (adjusted to a pH 5.5 with hydrochloric acid). About 0.5 grams of RHOZYME-54 (a protease manufactured by Rohm & Haas Company, Philadelphia, Pa.) was then added. The slurry was maintained at 45°-50° C. for 5 hours, and then heated to 90° C. for 10 minutes to inactivate the enzyme. The slurry was then centrifuged. The hazy effluent was treated with 1-2% activated carbon (dry basis) at 60° C. for about 30 minutes and then filtered with the aid of diatomaceous earth, producing a clear brown filtrate of soy hydrolysate.

Seventy-five ml of the soy hydrolysate containing 7.16 grams of dissolved solids were passed through a 2.54 cm × 35.6 cm column of Amberlite XAD-16 resin (185 ml bed volume) at 3-5 ml per minute, followed by a water wash. When the solids content of the effluent had dropped to zero, as determined by its refractive index, the collected effluent (360 ml, colorless, slightly hazy, pH 5.6) was freeze-dried to produce a white powder (Fraction 1).

The column was then washed with 88% methanol until the effluent showed no solids. The brown colored effluent was evaporated to remove the alcohol and the aqueous concentrate was freeze dried to yield a tan/brown powder (Fraction 2).

EXAMPLE 11

The corn gluten hydrolysate of Example 1, the soy hydrolysate of Example 10, and the fractions derived from soy hydrolysate as described in Example 10 were tested for their ability to inhibit root formation of perennial rye-grass. One ml of aqueous dilutions of the samples was applied to 7 cm diameter Whatman No. 1 filter paper held in 100×15 mm petri dishes. Ten perennial ryegrass seeds were added, the dishes covered, sealed with parafilm and held for 16 hours at 25° C. with continuous lighting. The papers were then held at 11° C. in the dark for 8 hours. This lighting-temperature cycle was repeated for 14 days. Root length was then determined and expressed as a percentage of the untreated control. The results are shown on Table IX below.

TABLE IX

THE EFFECT OF CORN GLUTEN HYDROLYSATE OF EXAMPLE 1 (CGH-1) SOY HYDROLYSATE, AND FRACTIONS FROM SOY HYDROLYSATE (SH) OF EXAMPLE 10 ON THE ESTABLISHMENT OF PERENNIAL RYEGRASS

| Sample | Application Level (mg/dm$^2$) | Average Root Length (mm) | Percent of Control |
|---|---|---|---|
| Control | 0 | 52.3 | 100 |
| CGH-1 | 2.6 | 25.3 | 48 |
| SH | 2.6 | 43.4 | 83 |
| SH-Fraction 1 | 2.6 | 14.0 | 27 |
| SH-Fraction 2 | 2.6 | 19.4 | 37 |

As can be seen from Table IX above, soy hydrolysate was not as effective at preventing the establishment of perennial ryegrass as was the corn gluten hydrolysate of Example 1. The soy hydrolysate Fractions 1 and 2, however, were more effective in inhibiting root formation of perennial ryegrass than was the corn gluten meal hydrolysate of Example 1.

EXAMPLE 12. ENZYME HYDROLYSIS OF SOY PROTEIN

Fifty grams of PROFAM 90 (soy protein isolate manufactured by Grain Processing Corporation, Muscatine, Iowa) was slurried in 700 ml of water. The thick slurry was adjusted from pH 7.3 to pH 8.5 with 10% Ca(OH)$_2$. ALCALASE 2.4L (0.5 ml) was added and the slurry was continuously stirred at 55° C. The pH was maintained between pH 8 to 8.5 with Ca(OH)$_2$. When the pH had remained constant, the pH was adjusted to pH 6.5 with 10% v.v/ H$_3$PO$_4$ to precipitate calcium as Ca$_3$(PO$_4$)$_2$. After heating the slurry in a steam chest for 20 minutes to inactivate the enzyme, it was filtered with filteraid and the residue discarded. The clear tan filtrate was freeze dried to a tan powder. The product contained 94.7% dry solids and 91.7% protein, as is, and was designated soy hydrolysate 1 (SH-1).

EXAMPLE 13. ENZYME HYDROLYSES OF WHEAT GLUTEN

Fifty grams of wheat gluten (Sigma Chemical Co., St. Louis, Mo.) was slurried in 500 ml of water and treated as described in Example 12. The resulting hydrolysate product was freeze dried to a tan powder containing 98.1% dry solids and 88.8% protein, as is, and was designated wheat hydrolysate, WH-1.

EXAMPLE 14

The above products of Examples 12-13, SH-1 and WH-1, along with corn gluten hydrolysate, CGH, prepared as described in Example 1, were assayed for their herbicide activity by the in vitro assay as described in Example 9. For the assay, dilutions of SH-1, WH-1, and CGH were prepared to contain 1.3, 2.6, 3.9 and 5.2 mg/dm$^2$. The results of the assay after 14 days are shown in Table X.

TABLE X

The Effects of Enzyme Hydrolysates of Corn Gluten (CGH), Soy Protein (SH-1), and Wheat Gluten (WH-1) on the Establishment of Perennial Ryegrass

| Application Level (mg/dm$^2$) | (% of Control Root Length) | | |
|---|---|---|---|
| | CGH | SH-1 | WH-1 |
| 0.0 | 100 | 100 | 100 |
| 1.3 | 100 | 90 | 69 |
| 2.6 | 21 | 43 | 47 |
| 3.9 | 0.3 | 0.6 | 18 |
| 5.2 | 0 | 0.9 | 1.8 |

As the data in Table X demonstrate, all protein hydrolysates contain significant levels of herbicide activity, especially at the 2.6 mg/dm$^2$ level and above. CGH appears to be the most effective, followed closely by SH-1, with WH-1 last. It is believed that other grain and plant proteins comprise herbicidal activity which could be isolated and concentrated in a similar fashion.

The invention has been described by reference to certain specific embodiments and detailed examples. However, as would be apparent to one of skill in the art, many modifications may be made while remaining within the spirit and scope of the invention.

What is claimed is:

1. A method for inhibiting growth of undesirable plants in a plot of soil comprising applying an amount of a plant protein hydrolysate to the plot of soil, prior to emergence of the unwanted plants, wherein said amount inhibits the growth of the undesirable plants by inhibiting their root development.

2. The method of claim 1 wherein the plant protein hydrolysate is selected from the group consisting of corn gluten hydrolysate, wheat gluten hydrolysate, soy protein hydrolysate and mixtures thereof.

3. The method of claim 1 wherein the plot of soil also comprises desirable plants.

4. The method of claim 3 wherein the plant protein hydrolysate is applied after the emergence of the desirable plants.

5. The method of claim 1 further comprising transplanting desirable plants into the plot of soil.

6. The method of claim 1 wherein the plant protein hydrolysate is applied at a concentration of about 0.5 g/dm$^2$ to 10 g/dm$^2$ of soil.

7. The method of claim 2 wherein the plant protein hydrolysate is corn gluten hydrolysate.

8. The method of claim 7 wherein the corn gluten hydrolysate has a protein content (dry basis) of at least about 50%.

9. The method of claim 8 wherein the corn gluten hydrolysate has a protein content (dry basis) of about 90%.

10. The method of claim 1 wherein the undesirable plants are broadleaf weeds.

11. The method of claim 1 wherein the undesirable plants are grassy weeds.

12. The method of claim 1 wherein the desirable plants are already established and are monocotyledonous.

13. The method of claim 11 wherein the desirable plants are turfgrasses.

14. The method of claim 1 wherein the desirable plants are dicotyledonous plants.

15. The method of claim 1 wherein the desirable plants are berry plants.

16. The method of claim 15 wherein the desirable plants are strawberries.

17. The method of claim 1 wherein the plant protein hydrolysate is dissolved or suspended in water and applied to the plot of soil by spraying or watering.

18. The method of claim 1 wherein the amount of plant protein hydrolysate is mixed with the soil.

19. An herbicidal composition comprising an herbicidally effective amount of a plant protein hydrolysate in combination with a compatible carrier vehicle.

20. The method of claim 19 wherein the plant protein hydrolysate is selected from the group consisting of corn gluten hydrolysate, wheat gluten hydrolysate, soy protein hydrolysate and mixtures thereof.

21. The composition of claim 19 wherein the carrier vehicle is a liquid vehicle.

22. The composition of claim 21 wherein the liquid vehicle is water.

23. The composition of claim 19 wherein the carrier vehicle is a solid.

* * * * *

UNITED STATES PATENT AND TRADEMARK OFFICE
CERTIFICATE OF CORRECTION

PATENT NO. : 5,290,749

DATED : March 1, 1994

INVENTOR(S) : Nick E. Christians et al.

It is certified that error appears in the above-identified patent and that said Letters Patent is hereby corrected as shown below:

On cover page, item [54], please delete --PORTEIN-- and insert "PROTEIN"

In Column 1, line 2, please delete --PORTEIN-- and insert "Protein"

Signed and Sealed this

Fifteenth Day of July, 1997

*Attest:*

BRUCE LEHMAN

*Attesting Officer*     *Commissioner of Patents and Trademarks*